United States Patent [19]

Gysling

[11] 3,980,654
[45] Sept. 14, 1976

[54] COPPER (II) COMPLEXES

[75] Inventor: Henry J. Gysling, Rochester, N.Y.

[73] Assignee: Eastman Kodak Company, Rochester, N.Y.

[22] Filed: Jan. 27, 1975

[21] Appl. No.: 544,096

Related U.S. Application Data

[62] Division of Ser. No. 409,828, Oct. 26, 1973, Pat. No. 3,880,724.

[52] U.S. Cl. .................... 260/270 PY; 96/48 R; 96/48 QP; 96/48 PD; 204/15; 260/270 TP; 260/270 D; 260/299; 260/326.15; 260/326.5 A; 260/326.8; 260/347.7; 260/438.1
[51] Int. Cl.² ................ C07F 1/08; C07D 213/00
[58] Field of Search .......... 260/438.1, 270 R, 326.8, 260/270 PY, 270 TP, 270 D, 249, 326.15, 326.5 A, 347.7

[56] References Cited

UNITED STATES PATENTS

| | | | |
|---|---|---|---|
| 2,792,334 | 5/1957 | Meguerian | 260/438.1 X |
| 2,924,551 | 2/1960 | Harwood et al. | 260/438.1 X |
| 2,924,552 | 2/1960 | Harwood et al. | 260/438.1 X |
| 2,977,279 | 3/1961 | Kasmin | 260/438.1 X |
| 3,859,092 | 1/1975 | Gysling et al. | 260/438.1 X |
| 3,860,500 | 1/1975 | Gysling | 260/438.1 X |
| 3,860,501 | 1/1975 | Gysling | 260/438.1 X |
| 3,880,724 | 4/1975 | Gysling | 260/438.1 X |

OTHER PUBLICATIONS

Chemical Abstracts, vol. 77, 69521c (1972).
Chemical Abstracts, vol. 72, 74222g (1970).

Primary Examiner—Helen M. S. Sneed
Attorney, Agent, or Firm—A. H. Rosenstein

[57] ABSTRACT

A novel copper (II) complex having the formula:

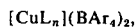

$$[CuL_n](BAr_4)_2,$$

wherein L is a monodentate or polydentate ligand, Ar is aryl containing from 6 to 12 carbon atoms, and $n$ is an integer of 2 or 4, is employed as an actinic radiation-sensitive component in an imaging process comprising imagewise-exposing a support carrying the copper (II) complex to actinic radiation and developing an image by direct printout or chemical or physical development. The complex has improved photographic speed and may be handled in room light prior to development.

10 Claims, No Drawings

COPPER (II) COMPLEXES

This is a division of application Ser. No. 409,828, filed Oct. 26, 1973, now U.S. Pat. No. 3,880,724.

This invention relates to photography, and more particularly to a novel copper (II) complex and a process of forming images in an actinic radiation-sensitive element comprising exposing a support carrying the photosensitive copper (II) complex to actinic radiation and developing the resulting image.

U.S. Pat. No. 3,658,534 issued Apr. 25, 1972, describes photosensitive polymers comprising simple metal salts bonded to oxygen, sulfur, phosphorous, nitrogen or halogen atoms by coordination bonds.

Thermographic copy sheets incorporating certain copper (I) complexes as the heat-sensitive component are described in U.S. Pat. No. 3,505,093 issued Apr. 7, 1970. This patent describes the imagewise exposure to heat of certain complexes to produce an image.

German Pat. No. 950,428 issued Oct. 11, 1956, describes the use of certain copper salts such as cuprous chloride as photosensitive compounds. These salts are, however, insensitive to light in the dry state and must be moistened to provide light sensitivity. Further, the copper (I) salts are unstable in air.

The use of cuprous oxide as a photosensitive compound has been disclosed in British Pat. No. 1,306,362. This compound, however, is not photosensitive to light unless moistened, is not colorless, and leaves an undesirable background with poor image differential.

No class of copper compounds has been found in the prior art that (1) will form a well-defined image after (a) imagewise exposure to actinic light at comparative high speed and (b) development, (2) can be handled in normal room light, (3) can be exposed in a dry state, and (4) is stable to humidity and oxidation in the atmosphere.

It is appreciated that the photosensitive copper materials of the prior art are exceedingly slow-speed in that they must be exposed to light or radiation for a long time in order to obtain a developable image. A common photographic speed for prior-art copper materials is $10^6$ ergs/cm.$^2$. The novel copper (II) complexes of this invention are high-speed in comparison with other copper materials, and in most instances reach projection speed range which is less than $10^3$ ergs/cm.$^2$.

The preparation of printed circuits has generally comprised the imagewise exposure of a photoresist material followed by removal of exposed or unexposed areas and etching and subsequent electroplating. This method is expensive, it does not allow for room-light handling, the raw stock is generally unstable, the bleaching or etching steps pose solution disposal problems, and a multitude of process steps in a great deal of equipment is required.

Accordingly, it is an object of this invention to provide a method of exposing a photosensitive copper material and developing an image that is resistant to oxidation and stable in the presence of moisture.

It is another object of this invention to provide novel copper (II) complexes.

Still another object of this invention is to provide novel copper (II) complexes which form images after high-speed, imagewise exposure to actinic light and physical or chemical development.

It is another object of this invention to provide novel copper (II) complexes which form printout images after imagewise exposure to actinic light.

It is another object of this invention to provide a method of imagewise-exposing copper (II) complexes to actinic light to form catalytic centers for development employing physical developers or chemical developers.

Still another object of this invention is to provide copper (II) complexes that have sensitivity essentially restricted to the UV region allowing their imagewise exposure to actinic radiation and development under ambient lighting conditions.

Still an additional object of this invention is to provide printed circuits by coating a support with a photosensitive copper (II) complex, exposing imagewise to actinic light, and developing the exposed portions of the element by physical development of the latent image.

These objects of the invention are accomplished by employing a novel, actinic, radiation-sensitive copper (II) complex represented by the formula $[CuL_n](BAr_4)_2$, wherein L is a ligand, Ar is aryl, and $n$ is 2 or 4, as the actinic, radiation-sensitive component in a process comprising imagewise-exposing a support carrying the described copper (II) complex to actinic light and developing the resulting image by printout or chemical or physical development.

The novel copper (II) complex is represented by the formula $[CuL_n](BAr_4)_2$, wherein L is a ligand selected from the group consisting of monodentate or polydentate neutral Lewis bases containing nitrogen or oxygen donor atoms; Ar is aryl containing from 6 to 12 carbon atoms such as phenyl, tolyl, naphthyl, anthryl, ethylphenyl and the like; and $n$ is an integer of 2 or 4.

Some examples of $BAr_4$ are:
tetraphenylborate,
tetra-o-tolylborate,
tetra-m-tolylborate,
tetra-p-tolylborate,
tetra-p-ethylphenylborate,
tetra-p-propylphenylborate,
tetra-3,4,5-trimethylphenylborate,
tetra-m-methyoxyphenylborate,
tetra-p-methoxyphenylborate,
tetra-p-ethoxyphenylborate,
tetra-p-bromophenylborate,
tetra-m-chlorophenylborate,
tetra-p-chlorophenylborate,
tetra-2,3,4,5-tetrachlorophenylborate,
tetra-m-fluorophenylborate,
tetra-p-fluorophenylborate,
tetra-m-trifluoromethylphenylborate,
tetra-p-trifluoromethylphenylborate,
tetraperfluorophenylborate,
tetra-p-dimethylaminophenylborate,
tetra-p-acetamidophenylborate,
tetra-4-biphenylborate,
tetra-3-phenoxyphenylborate,
tetra-1-naphthylborate,
tetra-2-naphthylborate,
tetra-9-anthrylborate,
tetra-9-phenanthrylborate,
tetra-2-phenylethynylborate,
tetra-1-pyrrolylborate,
tetrapyrazol-1-ylborate,
tetra-1-indolylborate,
tetra-2-furylborate,
tetra-5-methyl-2-furylborate,
tetra-2-thienylborate,
tetra-2-selenylborate, and the like.

L is either a monodentate ligand containing a nitrogen or oxygen donor atom wherein $n$ equals 4 or a bidentate or tridentate ligand containing nitrogen or oxygen donor atoms wherein $n$ equals 2.

The term "neutral Lewis bases" as employed herein is intended to mean uncharged electron donors such as methylamine, ethylenediamine, pyridine N-oxide, and the like.

The complexes wherein L is a bi- or tridentate ligand containing nitrogen donor atoms incorporated in an unsaturated conjugated molecule are generally useful in direct printout elements. These ligands are generally referred to as Class $b$ ligands A complete discussion of Class $b$ ligands may be found in J. L. Burmeister, *Coord. Chem. Rev.*, 1, 205 (1966), and R. G. Pearson, *J. Chem. Education*, 45, 581, 643 (1968).

The two classes of compounds of the general formula used in this invention are employed to advantage in printout systems consisting of copper (II) complexes with unsaturated polydentate ligands containing nitrogen donor atoms wherein $n$ is 2, such as 1,10-phenanthroline and 2,2'-bipyridine, and physically developable or chemically developable copper (II) complexes with saturated mono- or polydentate ligands containing oxygen or nitrogen donor atoms which, upon being exposed to radiation, produce photodecomposition products which are catalysts for various physical and chemical developers.

Useful Class $b$ unsaturated bidentate ligands include those having the formula:

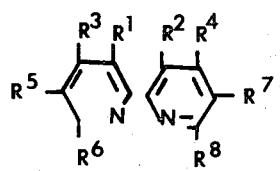

wherein each of $R^1$, $R^2$, $R^3$, $R^4$, $R^5$, $R^6$, $R^7$ and $R^8$ can independently be hydrogen, alkyl from 1 to 5 carbon atoms such as methyl, ethyl, propyl, butyl and pentyl, nitro, or halogen such as chloro or bromo. Additionally, each of $R^3$ and $R^4$ can be aryl such as phenyl, naphthyl and the like, $R^1$ and $R^2$ taken together can represent a vinylene group such as propylene, butylene and the like, $R^5$ and $R^6$ taken together can represent a 2-butenylene group, and $R^7$ and $R^8$ taken together can represent a 2-butenylene group.

Some examples of bidentate Class $b$ ligands useful herein are 1,10-phenanthroline, 2,9-dimethyl-4,7-diphenyl-1,10-phenanthroline, 2,9-dimethyl-1,10-phenanthroline, 2,2'-biquinoline, 2,2'-bipyridine and the like.

Representative unsaturated tridentate ligands such as 2,2',2''-terpyridine are described in the technical bulletin, *The Copper Reagents: Cuproine, Neocuproine, Bathocuproine*, published by G. Fredrick Smith Chemical Company, Columbus, Ohio (1958), and W. R. McWhinnie and J. P. Miller, *Advan. Inorg. Radiochem.*, 12, 135 (1969).

The ligands that form complexes which may be either physically or chemically developed can be monodentate, bidentate or tridentate Class $a$ ligands containing nitrogen or oxygen donor atoms. The donor atoms are generally incorporated in saturated molecules.

A complete discussion of Class $a$ ligands may also be found in J. L. Burmeister, *Coord. Chem. Rev.*, 1, 205 (1966), and R. J. Pearson, *J. Chem. Education*, 45 (1968).

Useful monodentate ligands generally have the formula $WR^9{}_3$, wherein W is a nitrogen donor atom and $R^9$ is a lower alkyl radical preferably containing 1 to 4 carbon atoms such as methyl, ethyl, propyl and butyl, or aryl preferably containing from 6 to 12 carbon atoms such as phenyl, tolyl, anthryl, phenylbutyl, naphthyl and the like.

Useful oxygen-containing monodentate ligands comprise, for example, N-oxides and P-oxides including pyridine N-oxide and triphenylphosphene oxide.

It is understood that the terms "alkyl" and "aryl" throughout this application include substituted alkyl and substituted aryl such as chloromethyl, bromophenyl, phenylbutyl, octylphenyl and the like. The only limitation is that the substituent cannot adversely affect the photosensitivity of the complex.

Useful monodentate, saturated ligands include those having the formula:

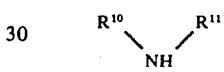

wherein each of $R^{10}$ and $R^{11}$ is independently selected from hydrogen, alkyl containing from 1 to 5 carbon atoms such as methyl, ethyl, propyl, butyl and pentyl, cycloalkyl such as cyclopentyl and cyclohexyl, and heterocyclic groups such as 2-pyridyl, 4-pyridyl, 3-methyl-4-pyridyl, 4-methyl-2-pyridyl, 2-quinolyl, 2-pyrrolidyl, and the like.

Bidentate saturated ligands include ligands having the formula:

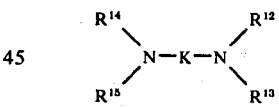

wherein K is alkylene from 1 to 5 carbon atoms such as 2-methyltrimethylene, ethylene and the like or cycloalkylene such as 1,2-cyclohexylene, and each of $R^{12}$, $R^{13}$, $R^{14}$ and $R^{15}$ are independently selected from the group consisting of hydrogen, alkyl having 1 to 5 carbon atoms such as methyl, ethyl, propyl, butyl and pentyl, and cycloalkyl such as cyclobutyl and cyclohexyl.

Other bidentate ligands useful herein include amine oxides such as 2,2'-bipyridine-N,N-dioxide and the like, as well as the mono-N-oxide of 2,2'-bipyridine. Examples of these ligands are found in A. N. Speca et al, *Inorg. Chem.*, 12, 1221 (1973).

Useful tridentate saturated ligands include compounds having the formula:

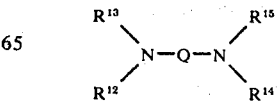

wherein each of $R^{12}$, $R^{13}$, $R^{14}$ and $R^{15}$ is as described above and Q is N-heteroalkylene of 3 to 5 carbon atoms such as 3-azapentamethylene and the like. Examples of these are diethylenetriamine, tetraethyldiethylenetriamine and the like.

L can be a mixture of different ligands if desired.

As previously pointed out, certain of the copper (II) complexes after imagewise exposure will print out directly. Examples of these complexes are [Cu(1,10-phenanthroline)$_2$][B(C$_6$H$_5$)$_4$]$_2$ and [Cu(2,2'-bipyridine)$_2$][B(C$_6$H$_5$)$_4$]$_2$ and the like.

Examples of photosensitive copper (II) complexes which may be developed by chemical or physical development include [Cu(H$_2$NCH$_2$CH$_2$NH$_2$)$_2$][B(C$_6$H$_5$)$_4$]$_2$ and [Cu(H$_2$NCH$_2$CH$_2$NHCH$_2$CH$_2$NH$_2$)$_2$][B(C$_6$H$_5$)$_4$]$_2$ and the like.

The complexes which may be exposed to actinic light and developed to form a metallic image may be prepared by a number of known methods. One general method is to complex a copper salt such as copper halide with an appropriate ligand and then introduce a solution of a salt of an anion such as [NaB(C$_6$H$_5$)$_4$], which imparts photosensitivity to the complex.

The primary method of obtaining the copper (II) complexes is to react (a) a solution of ligand in a solvent, such as ethanol or other useful alcohols and the like, acetonitrile and water with (b) copper (II) salts such as the chloride, perchlorate or nitrate by merely mixing the materials and then precipitating the desired complex by addition of an aqueous solution of NaB(C$_6$H$_5$)$_4$, filtering, and drying. An example is [Cu(ethylenediamine)$_2$][B(C$_6$H$_5$)$_4$]$_2$ which is prepared by adding excess ethylenediamine to an aqueous solution of CuCl$_2$ or Cu(NO$_3$)$_2$, followed by an addition of an aqueous solution of NaB(C$_6$H$_5$)$_4$ to precipitate the water-insoluble product [Cu(ethylenediamine)$_2$][B(C$_6$H$_5$)$_4$]$_2$. No special reaction conditions are necessary and the reaction can be carried out from 0° to 50° C. The products are readily soluble in polar organic solvents such as acetone and acetonitrile.

Generally, the copper salt and ligand may be reacted using any proportions, but it is preferred to add from about 0.1 to about 1.0 mole of copper salt for every mole of ligand.

The photosensitive complex may be either in a support or on the support in a hydrophilic binder prior to imagewise exposure. For example, the described complex can be imbibed into the support or coated on it. The substrate may be dipped in a bath of the complex and dried to render the element photosensitive. A method which is specifically useful in forming printed circuits comprises adding the complex to a binder solution and coating the resulting solution onto the substrate by any means, such as dip-coating, brushing, rolling, spraying or the like, and then drying.

The binder used as a vehicle for the photosensitive complex may be any of the hydrophilic binders used in photographic elements, including natural materials such as gelatin, albumin, agar-agar, gum arabic, alginic acid, etc., and synthetic materials such as polyvinyl alcohol, polyvinyl pyrrolidone, cellulose ethers, partially hydrolyzed cellulose acetate, acetylated cellulose acetate (cellulose acetate type S), and the like. Useful binders are described, for example, in the *Product Licensing Index*, Vol. 92, Dec., 1971, Publication 9232, p. 108, par. VIII. It is understood that, although many binders may be used herein, the binder should not absorb appreciably in the region of sensitivity of the complex. The complex may be used with varying amounts of binder material. Preferably, the complex-to-binder weight ratio is from about 3:1 to about 1:2.

The complex may be either imbibed into or coated onto any support typically used for photographic elements. Support materials used herein are subject to wide variation. Glass may be employed, as may be metals such as aluminum, copper, zinc and tin. Conventional film bases such as cellulose acetate, cellulose nitrate, cellulose acetate butyrate, poly(ethylene terephthalate), polystyrene and paper, including polyethylene-coated paper and polypropylene-coated paper, are also used. If the complex is to be imbibed into the support, the solution generally contains from 0.001 mole to 1 mole of the copper (II) complex per liter and porous support materials such as paper should be used. The preferred support materials, when the process is to be used to form an element for use as a printed circuit, are poly(ethylene terephthalate), polyimides and cellulose acetate.

The coated support is dried and may then be stored for convenient periods of time prior to imagewise exposure, since the complexes are not adversely affected by ambient light or by other typical storage conditions such as the humidity in the atmosphere.

The elements are typically exposed through a pattern of actinic radiation providing a latent image in the exposed areas. The complexes are sensitive to actinic light such as ultraviolet rays generally in the wavelength range of 1800 to 4000 angstroms. Many sources of ultraviolet light may be used such as high-vapor mercury lamps, carbon arc lamps and the like. The complexes may generally be exposed for at least 5 seconds and preferably from 5 to about 60 seconds.

The latent image in the exposed elements may either print out directly or it may be developed into a desired metal image, typically a visible image, by either physical development or chemical development.

The physical development may take place in any conventional physical developing bath. The physical development bath generally contains metal ions in salt form and a reducing agent for the metal ions. Typical physical developer solutions are well-known (see Hornsby, *Basic Photographic Chemistry*, (1956) 66, and Mees and James, ed., *The Theory of the Photographic Process*, 3rd edition (1966), 329–331, and U.S. Pat. No. 3,650,748 by Yudelson et al. issued Mar. 21, 1972) and contain the metallic ions such as silver, copper, iron, nickel or cobalt necessary to form a visible image at and in the vicinity of the nucleating centers.

The preferred metal salts employed as the source of metal for physical development are water-soluble salts such as silver nitrate, cupric salts such as copper chloride, copper nitrate, copper sulfate, copper formate, copper acetate and the like, and nickel salts such as nickel chloride, nickel bromide, nickel sulfate, nickel nitrate, nickel formate and the like.

Typical reducing agents used in the physical developer include, for example, polyhydroxy-substituted aryl compounds such as hydroquinones, catechols, and pyrogallols; ascorbic acid derivatives; aminophenols; p-phenylenediamines; and the like developing agents used in the photographic art. Particular examples of reducing agents for physical developer solutions are 2-methyl-3-chlorohydroquinone, bromohydroquinone, catechol, 5-phenylcatechol, pyrogallol monomethyl ether (1-methoxy-2,3-dihydroxybenzene), 5-methylpyrogallol monomethyl ether, isoascorbic acid, N-methyl-p-aminophenol, dimethyl-p-phenylenediamine, 4-amino-N,N-di(n-propyl)aniline and 6-amino-1-ethyl-1,2,3,4-tetrahydroquinoline. Borane reducing agents such as amineboranes, borohydride and the like may also be used.

The preferred physical development baths include the Copper Enthone developer baths (a trademark of Enthonics Corp.) containing copper sulfate, formaldehyde, Rochelle salt and nickel sulfate.

The physical developer solutions, in addition to the metal salt and reducing agent, can comprise a complexing agent for the metal salt such as Rochelle salt or other ligands for the metal salt, and can include a variety of other materials to facilitate maintenance and operation of the developer and to improve the quality of the developed image, such as acids and bases to adjust pH, buffers, preservatives, thickening agents, brightening agents and the like. The rate of development can be increased, and hence the time of development decreased, by adding to the developer solution a surfactant such as an alkyl metal salt of a sulfonated fatty acid, e.g., dodecyl sodium sulfonate.

The proportions in which the various components of the physical developer are present in the developer solution can vary over a wide range. Suitable concentrations of reducible heavy metal salt can range from about 0.01 mole to about 1.0 mole of metal salt per liter of solution. The upper limit of concentration is dependent upon the solubility of the particular metal salt employed. Preferably, the solution is about 0.1 molar to about 0.3 molar with respect to the heavy metal salt. The relative proportions of metal salt and complexing agent are dependent upon the particular heavy metal salt or salts and the particular complexing agent or agents which are employed. As a general rule, sufficient complexing agent should be incorporated to "tie up" the reducible heavy metal ions which are in solution and to lessen the tendency of these metal ions to be reduced prior to use of the developer solution. Depending upon the particular heavy metal salt and the particular complexing agent which is employed, the amount of complexing agent present typically can vary from about 0.2 mole to about 10 moles of complexing agent per mole of metal salt present. Typically, the reducing agent can be present in amounts from about 0.01 mole to about 5 moles of reducing agent per mole of metal salt present in the solution. In order to permit the developer solution to be utilized for its maximum life, at least one equivalent of reducing agent should be present in the solution for each equivalent of reducible heavy metal salt.

The physical developers are operative over a wide range of pH. However, since the borane reducing agents undergo an acid-catalyzed hydrolytic reaction which reduces their stability during storage, it is preferred that the physical developers be maintained at a moderately alkaline pH of about 8 to 11, and preferably of about 8.5 to 9.5. Nevertheless, the physical developers can be used under acidic conditions as low as pH 3 if such conditions are advantageous for the particular photographic process in which they are used. The physical developer solution can be brought to the desired pH by addition of an appropriate amount of a suitable base, for example, ammonium hydroxide or sodium hydroxide, and can be maintained at the desired pH by addition of a suitable buffering system, for example, sodium carbonate and sodium bicarbonate. Other materials which can be used to adjust the pH to the desired range and buffers which will maintain the pH in that range can be readily determined by those skilled in the art.

The exposed elements according to the invention may also be developed chemically, such as by immersing in solutions comprising a suitable developing agent. Useful developing agents include aminophenols, phenylenediamines, hydroquinones, aminodialkylanilines, heterocyclic chemical developers such as 1-phenyl-3-pyrazolidone, and the like. A description of chemical developer solutions which may be used herein can be found in Mees and James, *The Theory of the Photographic Process*, 3rd, ed., Chapter 13 (1966).

The process outlined above may yield a positive or negative image depending on the nature of the photosensitive complex used and the development process.

Development of an image according to the invention can be carried out under ambient conditions of temperature and pressure, such as at a temperature of about 20° to about 30° C. at atmospheric pressure.

The process of this invention is particularly useful in forming elements for use as printed circuits. In this method, insulating supports are either imbibed with the copper (II) complexes or coated with the complexes in a binder and dried. The coated supports are imagewise-exposed to actinic light so that the exposed portions are catalytic to the physical deposition of a metal such as copper, silver or nickel by physical development. The exposed element is then physically developed in a metal salt-containing bath such as in a copper physical development bath, and the metal such as copper is deposited and built up on the exposed portions of the element only. The element may then be dried and, if desired, a heavier buildup of metal may be achieved in the exposed areas by electroplating over the element. The completed element may then be used to form a printed circuit.

The following examples are included for a further understanding of the invention.

EXAMPLE 1

A photosensitive complex was formed by adding a solution of 3.42 g. of $NaB(C_6H_5)_4$ in 60 ml. water to a solution of 2.73 g. $Cu(H_2NCH_2CH_2NH_2)_2Cl_2.H_2O$ in 10 ml. water. A pale purple precipitate was formed and filtered, washed with water and dried under vacuum over $P_2O_5$ for 24 hr. The analysis for the solid complex having the formula $Cu(H_2NCH_2CH_2NH_2)_2[B(C_6H_5)_4]_2$ which had a melting point of 89° C. is:

Calc'd: C, 75.90; H, 6.87; N, 6.82; B, 2.63. Found: C, 75.1; H, 6.9; N, 6.9; B, 2.6.

EXAMPLE 2

A photosensitive complex was formed by adding 4 ml. of 1,3-propanediamine to a solution of 1.7 g. of $CuCl_2.2H_2O$ in 40 ml. $H_2O$. After dilution to 500 ml. with $H_2O$, a solution of 6.8 g. of $NaB(C_6H_5)_4$ in 150 ml. $H_2O$ was added to form a blue precipitate. The solid was filtered, washed with water and ligroin, and vacuum-dried over $P_2O_5$ for 24 hr. The resulting complex having the formula $Cu(H_2NCH_2CH_2CH_2NH_2)_2[B(C_6H_5)_4]_2$ had the following analysis:

Calc'd: C, 76.22; H, 7.11; N, 6.59; B, 10.08. Found: C, 76.9; H, 7.4; N, 6.5; B, 9.2.

EXAMPLE 3

A photosensitive copper (II) complex was prepared by adding 5 ml. of diethylenetriamine to a solution of 3.4 g. $CuCl_2.2H_2O$ in 500 ml. $H_2O$. Upon addition of a solution of 13.7 g. of $NaB(C_6H_5)_4$ in 300 ml. $H_2O$, a blue solid precipitated which was filtered, washed with $H_2O$ and ligroin, and vacuum-dried over $P_2O_5$ for 20 hr. The resulting copper (II) complex having the formula $Cu(H_2NCH_2NHCH_2CH_2NH_2)_2[B(C_6H_5)_4]_2$ had the following analysis:

Calc'd: C, 73.9; H, 7.32; N, 9.25; B, 2.38. Found: C, 73.2; H, 7.2; N, 9.3; B, 2.3.

EXAMPLE 4

A photosensitive complex was formed by adding 5 ml. of 1,2-propanediamine to a solution of 1.7 g. of $CuCl_2.2H_2O$ in 40 ml. $H_2O$. After dilution to 500 ml. with $H_2O$, a solution of 6.8 g. of $NaB(C_6H_5)_4$ in 150 ml. of $H_2O$ was added to form a blue precipitate. The solid was filtered, washed with water and ligroin, and vacuum-dried over $P_2O_5$ for 24 hr. The resulting complex having the formula $Cu[H_2NCH_2CH(CH_3)NH_2]_2[B(C_6H_5)_4]_2$ had the following analysis:

Calc'd: C, 76.22; H, 7.11; N, 6.59; B, 2.55. Found: C, 75.8; H, 7.4; N, 6.4; B, 2.3.

EXAMPLE 5

A photosensitive complex was formed by adding 4 ml. of N,N-diethylethylenediamine to a solution of 1.7 g. of $CuCl_2.2H_2O$ in 40 ml. $H_2O$. After dilution to 500 ml. with $H_2O$, a solution of 6.8 g. of $NaB(C_6H_5)_4$ in 150 ml. of $H_2O$ was added to form a blue precipitate. The solid was filtered, washed with water and ligroin, and vacuum-dried over $P_2O_5$ for 24 hr. The resulting complex having the formula $Cu[(C_2H_5)_2NCH_2CH_2NH_2]_2[B(C_6H_5)_4]_2$ had the following analysis:

Calc'd: C, 77.06; H, 7.77; N, 6.00; B, 2.31. Found: C, 75.3; H, 7.6; N, 5.9; B, 2.0.

EXAMPLE 6

A photosensitive complex was formed by adding 4 ml. of 1,2-diaminocyclohexane to a solution of 1.7 g. of $CuCl_2.2H_2O$ in 40 ml. $H_2O$. After dilution to 500 ml. with $H_2O$, a solution of 6.8 g. of $NaB(C_6H_5)_4$ in 150 ml. $H_2O$ was added to form a blue precipitate. The solid was filtered, washed with water and ligroin, and vacuum-dried over $P_2O_5$ for 24 hr. The resulting complex having the formula:

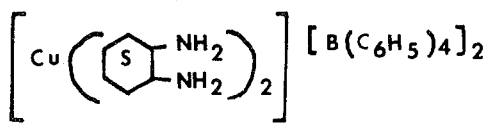

had the following analysis:

Calc'd: C, 77.38; H, 7.37; N, 6.02; B, 1.16. Found: C, 77.0; H, 7.3; N, 5.6; B, 1.5.

EXAMPLE 7

A photosensitive complex was formed by reacting 175 ml. of a warm 50% water-ethanol solution containing 2.3 g. $Cu(2,2'\text{-bipyrydine})_2(ClO_4)_2$ with 30 ml. of an aqueous solution containing 1.5 g. $NaB(C_6H_5)_4$. The pale green product was filtered, washed with ethanol and ether, and dried under vacuum. The resulting copper (II) complex had the formula $Cu(2,2'\text{-bipyrydine})_2[B(C_6H_5)_4]_2$ and the following analysis:

Calc'd: C, 80.44; H, 5.57; N, 5.52; B, 2.13. Found: C, 79.4; H, 6.0; N, 6.5; B, 1.5.

EXAMPLE 8

A solution of the copper (II) complex of Example 7 in 10 ml. acetonitrile was imbibed into a paper support and imagewise-exposed to ultraviolet light for 10 sec. under a 350-watt Gates lamp. A dark brown, negative printout image appeared in the exposed region. A similar image was produced after imagewise-exposing to UV light for 10 sec. under an 8-watt GE F815BL light.

EXAMPLE 9

A solution of 0.75 g. of the complex of Example 1 was dissolved in 20 ml. acetone and imbibed into a paper support. After a 5-min. imagewise exposure to UV light under a 350-watt Gates lamp, the imbibed support was immersed in a nickel physical development bath comprising 50 ml. $H_2O$, 1.6 g. dimethylamine borane and 100 ml. of a concentrate formed from 213 g. of nickel chloride, 28.8 g. citric acid, and 164 g. ethanolamine dissolved in water to a volume of 4 liters. Physical development occurred in the exposed regions with no fogging in the unexposed regions.

EXAMPLE 10

The coated paper of Example 9 was imagewise-exposed to UV light for 2 min. under a 350-watt Gates lamp and developed in the same development bath as Example 9 with the exception that the amount of dimethylamine borane in the developer was raised to 5% by weight. A heavy black coating was achieved in the exposed regions.

EXAMPLE 11

The coated paper of Example 9 was imagewise-exposed to UV light for 5 min. under a 350-watt Gates lamp and physically developed in the commercially available Enplate copper development bath. A negative image was obtained.

EXAMPLE 12

The coated paper of Example 9 was imagewise-exposed to UV light for 5 sec. under a 360-watt Gates lamp and immersed in a nickel physical developer consisting of 40 mg. of hydrazinebisborane and 100 ml. of a stock solution containing 68.75 g. $NiCl_2.6H_2O$, 45 g. ethylenediamine and 225 g. $KCH_3CO_2$ mixed with water to a final volume of 3 liters. A black image was developed in the exposed areas only. The latent image was stable for at least 1 wk. prior to development and the complex was found to be sensitive for subsequent development in the range of 230 m$\mu$ to 400 m$\mu$.

EXAMPLE 13

A film of the complex of Example 1 was prepared by dissolving 1 g. of the complex in 30 ml. of a 10% by weight solution of 30% acetylated cellulose acetate in 50—50 (v/v) acetone-methoxyethanol. The binder solution was coated on unsubbed cellulose acetate film base and imagewise-exposed to UV light for 15 sec. under a 360-watt Gates lamp. The exposed film was immersed in a nickel physical developer consisting of 40 mg. of hydrazinebisborane in 100 ml. of the nickel stock solution described in Example 12. A black negative image was obtained.

EXAMPLE 14

A solution of 1 g. of the complex of Example 2 in 20 ml. acetone was imbibed into a paper support. The paper support was imagewise-exposed to UV light under a 360-watt Gates lamp and developed in the nickel physical developer solution described in Example 9. A black image was achieved.

EXAMPLE 15

A paper support was imbibed with a solution of 1 g. of the copper (II) complex of Example 3 in 25 ml. acetone and imagewise-exposed to UV light for 30 sec. under a 360-watt Gates lamp. The resulting image was physically developed by immersing in a nickel physical developer consisting of 50 mg. hydrazinebisborane in 50 ml. of a solution containing 68.75 g. $NiCl_2 \cdot 6H_2O$, 45 g. ethylenediamine and 225 g. $KCH_3CO_2$ and mixed with water to obtain a final volume of 3 liters.

EXAMPLE 16

A paper support was imbibed with a solution of 1 g. of the complex of Example 4 in 30 ml. acetone. After imagewise-exposing to UV light for 30 sec. under a 360-watt Gates lamp, a black image was obtained by immersing in the nickel physical developer of Example 9.

EXAMPLE 17

A film was prepared by dissolving 0.7 g. of the complex of Example 4 in 25 ml. of a 10% by weight solution of 30% acetylated cellulose acetate in a 50—50 (v/v) solution of acetone-2-methoxyethanol and coating the binder solution on a gelsubbed poly(ethylene terephthalate) support.

The coated film was imagewise-exposed to UV light for 10 sec. under a 360-watt Gates lamp. A black image was developed by immersing in a physical developer consisting of 30 mg. hydrazinebisborane in 50 ml. of the nickel stock solution described in Example 12.

A heavy overcoat of copper was deposited on the nickel coating by further immersing the film in the copper development bath described in Example 11.

EXAMPLE 18

A paper support was imbibed with a solution of 1 g. of the complex of Example 5 in 30 ml. acetone and imagewise-exposed to UV light for 60 sec. A black image was achieved by immersing in the nickel physical development bath of Example 9.

EXAMPLE 19

A paper support was imbibed with a solution of 1 g. of the complex of Example 5 in 30 ml. acetone. After imagewise exposure to UV light for 60 sec. under a 360-watt Gates lamp, a black image was developed by immersing in the nickel developer of Example 9.

EXAMPLE 20

A binder solution comprising 0.5 g. of $Cu[H_2NCH_2CH_2NH_2]_2[B(C_6H_5)_4]_2$ and 10 ml. of a cellulose acetate type S solution (10%) was coated onto a poly(ethylene terephthalate) support at a wet thickness of 0.006 inch.

A printed circuit was prepared by imagewise-exposing the dry element to a low-pressure mercury arc through a stainless-steel mask for 3 min. The resulting image was physically developed in a Copper Enthone plating bath for 30 min. at 32° C. A 5-micron, electrically conducting image appears at the exposed portion. The image was capable of being electroplated with additional copper to produce a thicker conductor.

Although the invention has been described in considerable detail with reference to certain preferred embodiments thereof, it will be understood that variations and modifications can be effected without departing from the spirit and scope of the invention as described hereinabove.

We claim:

1. A copper (II) complex having the formula:

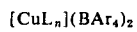

wherein L is a ligand selected from the group consisting of monodentate or polydentate neutral Lewis bases containing a nitrogen or oxygen donor atom, Ar is aryl containing from 6 to 12 carbon atoms, and $n$ is 4 when L is a monodentate ligand and $n$ is 2 when L is a polydentate ligand.

2. The complex of claim 1 wherein Ar is phenyl.

3. The complex of claim 1 wherein L is a bidentate or tridentate Class $b$ ligand having nitrogen donor atoms.

4. The complex of claim 1 wherein L is an unsaturated bidentate or tridentate Class $b$ Lewis base containing nitrogen donor atoms and wherein $n$ is 2.

5. The complex of claim 1 wherein L is a saturated mono-, bi- or tridentate Class $a$ Lewis base containing nitrogen or oxygen donor atoms and wherein $n$ is 4 when L is a bi- or tridentate ligand and $n$ is 2 when L is a monodentate ligand.

6. A copper (II) complex having the formula:

7. A copper (II) complex having the formula:

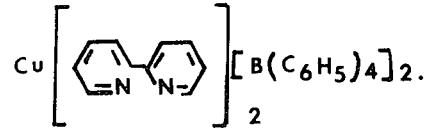

8. The complex having the formula:

9. A copper (II) complex having the formula:

10. A copper (II) complex having the formula:

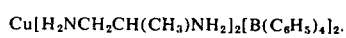

* * * * *